United States Patent
Huang et al.

(10) Patent No.: US 8,062,465 B1
(45) Date of Patent: Nov. 22, 2011

(54) METHODS FOR IMPROVED STENT RETENTION

(75) Inventors: Bin Huang, Pleasanton, CA (US); Daniel Castro, Santa Clara, CA (US); David C. Gale, San Jose, CA (US); Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1111 days.

(21) Appl. No.: 11/890,170

(22) Filed: Aug. 2, 2007

Related U.S. Application Data

(60) Provisional application No. 60/835,295, filed on Aug. 2, 2006.

(51) Int. Cl.
*B29C 65/00* (2006.01)

(52) U.S. Cl. ............... 156/308.2; 156/294; 606/194; 623/1.11

(58) Field of Classification Search ............... 156/308.2, 156/293, 294, 309.6; 623/1.11, 1.12; 606/194, 606/195, 198
See application file for complete search history.

(56) References Cited

U.S. PATENT DOCUMENTS

| | | | | |
|---|---|---|---|---|
| 5,163,952 A | * | 11/1992 | Froix | 623/1.18 |
| 5,421,955 A | * | 6/1995 | Lau et al. | 216/48 |
| 5,817,100 A | * | 10/1998 | Igaki | 623/1.11 |
| 6,063,092 A | * | 5/2000 | Shin | 606/108 |
| 6,245,076 B1 | | 6/2001 | Yan | |
| 6,666,880 B1 | * | 12/2003 | Chiu et al. | 623/1.11 |
| 6,682,553 B1 | * | 1/2004 | Webler, Jr. | 623/1.11 |
| 6,743,251 B1 | * | 6/2004 | Eder | 623/1.11 |
| 6,958,073 B2 | | 10/2005 | Rogers et al. | |
| 7,198,637 B2 | | 4/2007 | Deshmukh et al. | |
| 2006/0047336 A1 | | 3/2006 | Gale et al. | |
| 2007/0271763 A1 | | 11/2007 | Huang et al. | |
| 2007/0282433 A1 | | 12/2007 | Limon et al. | |
| 2007/0289117 A1 | | 12/2007 | Huang et al. | |
| 2008/0016668 A1 | | 1/2008 | Huang et al. | |
| 2008/0033523 A1 | | 2/2008 | Gale et al. | |
| 2008/0033524 A1 | | 2/2008 | Gale | |

OTHER PUBLICATIONS

Michelman "Michem Prime Dispersions" 2006.*
U.S. Appl. No. 11/326,797, filed Jan. 6, 2006, Abbate et al.
U.S. Appl. No. 11/330,927, filed Jan. 11, 2006, Wu et al.

* cited by examiner

*Primary Examiner* — John Goff, II
(74) *Attorney, Agent, or Firm* — Squire Sanders & Dempsey, (US) LLP

(57) ABSTRACT

Methods for improved stent retention on an expandable member during delivery are disclosed. Methods include fabricating delivery systems including a retention layer over the stent, the expandable member, or both for improving retention of the stent on the expandable member during delivery.

4 Claims, 5 Drawing Sheets

METHODS FOR IMPROVED STENT RETENTION

CROSS REFERENCE TO RELATED APPLICATION

This application claims the benefit of and incorporates by reference U.S. Patent Application No. 60/835,295 which was filed on Aug. 2, 2006.

BACKGROUND OF THE INVENTION

1. Field of the Invention

This invention relates to implantable medical devices, such as stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In advancing a stent through a body vessel to a deployment site, the stent must be able to securely maintain its axial as well as rotational position on the delivery catheter without translocating proximally or distally, and especially without becoming separated from the catheter. Stents that are not properly secured or retained to the catheter may slip and either be lost or be deployed in the wrong location. The stent must be "crimped" in such a way as to minimize or prevent distortion of the stent and to thereby prevent abrasion and/or reduce trauma to the vessel walls.

Generally, stent crimping is the act of affixing the stent to the delivery catheter or delivery balloon so that it remains affixed to the catheter or balloon until the physician desires to deliver the stent at the treatment site. Current stent crimping technology is sophisticated. Examples of such technology which are known by one of ordinary skill in the art include a roll crimper; a collet crimper; and an iris or sliding-wedge crimper. To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth under this motion, and the diameter of the stent is reduced. The process can be broken down into more than one step, each with its own level of force, translational distance, and number of cycles. This process imparts a great deal of shear to the stent in a direction perpendicular to the catheter or catheter wall. Furthermore, as the stent is crimped, there is additional relative motion between the stent surface and the crimping plates.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet onto the collet stops crimps the stent to the known outer diameter. While this seems ideal, it can lead to problems. Stent struts have a tolerance on their thickness. Additionally, the process of folding non-compliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent or balloon damage.

In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. From the discussion on the collet crimper, there are advantages in applying a fixed level of force as variability in strut and balloon dimension will not change the crimping force. The sliding wedges impart primarily normal forces. As the wedges slide over each other, they impart some tangential force. Lastly, the sliding wedge crimper presents a nearly cylindrical inner surface to the stent, even as it crimps. This means the crimping loads are distributed over the entire outer surface of the stent.

Current stent crimping methods were developed for all-metal stents. Stent metals, such as stainless steel, are durable and can take abuse. When crimping is too severe, it usually damages the underlying balloon, not the metal stent. But polymeric stents present different challenges. A polymer stent requires relatively wider struts than metal stents so as to provide suitable mechanical properties, such as radial strength. At the crimping stage, less space is provided between the struts which can result in less effective stent retention than a metallic stent, increasing the likelihood of detachment of the stent or premature deployment of the stent in the body. Moreover, the use of a high processing temperature during the crimping process to enhance stent retention may not be possible as a polymeric stent may have a glass transition temperature generally equivalent to the glass transition temperature of the balloon. Higher processing temperatures may cause the stent to lose some of its preferred mechanical properties.

The present invention includes methods of improving stent retention during delivery for polymeric stent. Such methods can are also applicable to metallic stents.

SUMMARY OF THE INVENTION

Various embodiments of the present invention include a method of fabricating a stent delivery assembly, comprising:

providing a stent including a stent substrate with a retention layer comprising a polymeric material, the retention layer disposed over at least a portion of the substrate; disposing the stent over an expandable member, wherein the stent disposed on the expandable member comprises a delivery assembly; and heating the delivery assembly to increase the temperature of the retention layer, wherein the retention layer is heated to a temperature close to, at or above a Tm, a Tg or a Ts of the polymeric material of the retention layer, the retention layer facilitating adhesion of the stent to the expandable member. In certain embodiments, the retention layer is heated to a temperature well above the Tg.

Further embodiments, include a method of fabricating a stent delivery assembly, comprising: providing a stent including a stent substrate; disposing the stent over an expandable member, the expandable member including a retention layer comprising a polymeric material, the retention layer disposed over at least a portion of a surface of the expandable member, wherein the stent disposed on the expandable member comprises a delivery assembly; and heating the delivery assembly to increase the temperature of the retention layer, wherein the retention layer is heated to a temperature close to, at or above a Tm, a Tg or a Ts of the polymeric material of the retention layer, the retention layer facilitating adhesion of the stent to the expandable member. In certain embodiments, the retention layer is heated to a temperature well above the Tg.

Additional embodiments include a method of fabricating a stent delivery assembly, comprising: disposing a sheath over a stent, the stent comprising a stent substrate including a retention layer comprising a polymeric material, the retention layer disposed over at least a portion of the substrate; disposing the stent and the sheath over a central axial section of an expandable member, leaving a distal axial section and proximal axial section of the expandable member between the middle axial section uncovered by the stent and the sheath; inflating the distal axial section, wherein the distal axial section is heated; and inflating the proximal axial section, wherein the proximal axial section is heated, wherein the retention layer is heated to a temperature close to, at or above a Tm, a Tg or a Ts of the polymeric material of the retention layer, wherein the inflated distal axial section, inflated proximal axial section, and retention layer facilitate adhesion of the stent to the expandable member. In several embodiments, the retention layer is heated to a temperature well above the Tg.

Certain embodiments of the present invention include a method of fabricating a stent delivery assembly, comprising: disposing a sheath over a stent positioned over a support member, the sheath comprising a degradable or water soluble polymeric material, wherein the sheath fits loosely over the stent; and heating the sheath to cause the sheath to shrink radially over the stent so that the sheath can retain the stent on the support member during delivery of the stent within a bodily lumen.

Some additional embodiments of the present invention include a method of delivering a stent to an implant site in a bodily lumen, comprising: providing delivery system comprising a sheath disposed over a stent with the stent positioned over a support member, the sheath comprising a degradable or water soluble polymeric material configured to dissolve or erode upon exposure to bodily fluids, wherein the sheath retains the stent on the support member; and conveying the delivery system through a bodily lumen to an implant site, wherein the sheath dissolves or erodes during the delivery.

DETAILED DESCRIPTION OF THE INVENTION

Figure 1:
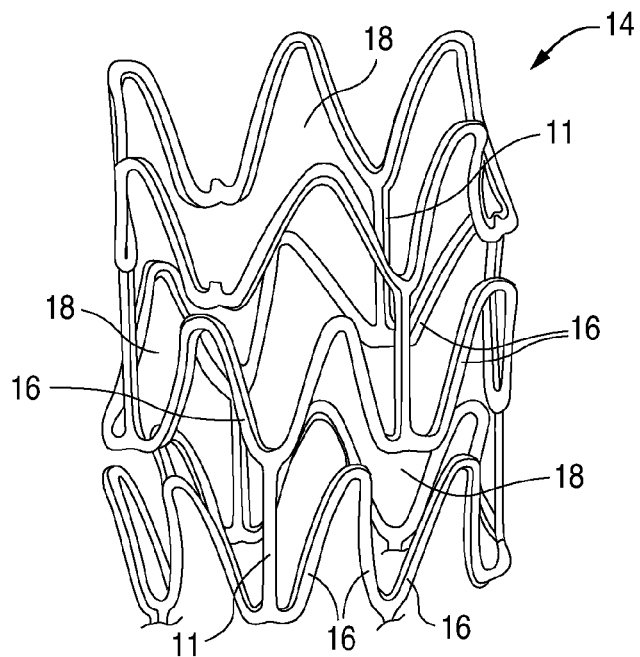
FIG. 1 depicts a stent.

Embodiments of the present invention include methods of stent retention on an expandable member or balloon. The stent crimping methods disclosed are suitable to adequately and uniformly crimp a balloon expandable stent onto a balloon or expandable member of a catheter assembly. The embodiments of the invention are also applicable to self-expandable stents and stent-grafts. In some embodiments, methods of the present invention are particularly directed to crimping of a biodegradable, polymeric stent on a balloon of a catheter assembly. A polymer stent has many advantages over metal stents, including the ability to be placed in the body only for the duration of time until the intended function of the stent has been performed. However, retention of a polymer stent has been proven to be more challenging than that of a metallic stent. Polymer stents can require wider struts than metal stents so as to provide suitable mechanical properties, such as material strength, for the stent. At the crimping stage, less space is provided between the struts which can result in worse stent retention than a metallic stent. Moreover, the use of high processing temperature during the crimping process to enhance stent retention may not be possible as a polymeric stent may have a glass transition temperature generally equivalent to the glass transition temperature of the balloon. Higher processing temperatures may cause the polymeric stent to lose some of its preferred mechanical properties.

Embodiments of the present invention include methods and delivery assemblies to improve stent retention or increase the security of attachment of a stent on a delivery balloon. Certain embodiments of the present invention include a retention layer or coating on a delivery stent, delivery balloon, or both a balloon and stent that improves or facilitates retention of the stent on the delivery balloon. In such embodiments, the retention layer can include a polymeric material having a lower glass transition temperature (Tg) or lower softening temperature (Ts) than the stent material below the retention layer. In some embodiments, the retention layer can include a polymeric material having a lower glass transition temperature (Tg) or lower softening temperature (Ts) than the base balloon material. The base balloon material refers the balloon wall or membrane structure apart from any coatings or layers.

In various embodiments of the present invention, the stent is crimped over the balloon at a temperature that softens, melts, or partially melts the retention layer on the stent, balloon, or both. The softened or melted retention layer acts as an adhesive between the stent and balloon. The retention layer improves or facilitates retention of the stent on the balloon during part or all of the delivery of the stent to a treatment site in a bodily lumen.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Melting temperature" (Tm) can refer to the approximate temperature at which a polymer transitions from a crystalline or semi-crystalline phase to a solid amorphous phase.

"Crimping temperature" can refer to the temperature of the crimping device, heating medium, stent, balloon, retention layer, or a combination thereof during the crimping process.

The softening temperature (Ts) can refer to the "Vicat Softening Temperature" (VST) which is a measure of the temperature at which a polymer starts to soften at specified test conditions according to ISO 306. It is determined with a standard indenter (a flat-ended needle of 1 mm² circular cross section) penetrating into the surface of a test specimen under a predefined load. The temperature at 1 mm penetration is quoted as the VST in ° C. VST gives an indication of a material's ability to withstand limited short-term contact with a heated object.

The structure of a stent is typically composed of scaffolding, substrate, or base material that includes a pattern or network of interconnecting structural elements often referred to in the art as struts or bar arms. Referring to FIG. 1, an exemplary stent 14 is illustrated. Stent 14 can include a plurality of struts 16 connected by linking struts 11, with interstitial spaces 18 located in between the struts. The plurality of struts 16 can be configured in an annular fashion in discrete "rows" such that they form a series of "rings" throughout the body of stent 14.

Figure 2A:
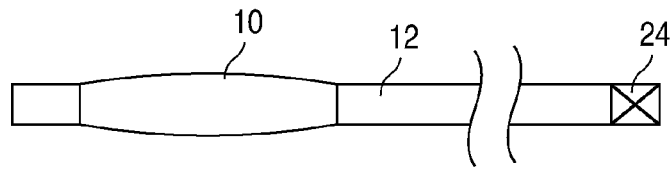
FIG. 2A depicts an expandable member.

FIG. 2A depicts an expandable member, such as a balloon 10, integrated at a distal end of a catheter assembly 12. In some embodiments, the balloon 10 is intended to include any type of enclosed member such as an elastic type member that is selectively inflatable to dilate from a collapsed configuration to a desired and controlled expanded configuration. The balloon 10 should also be capable of being deflated to a reduced profile or back to its original collapsed configuration. The balloon 10 can be made from any suitable type of material and can be of any thickness so long as the ability to crimp the stent onto the balloon and optimum performance capabilities of the balloon are not adversely compromised. Performance properties include, for example, high burst strength, good flexibility, high resistance to fatigue, an ability to fold, and ability to cross and re-cross a desired region of treatment or an occluded region in a bodily lumen, and a low susceptibility to defects caused by handling and crimping, among other possibilities.

The balloon is illustrated in FIG. 2A in a collapsed configuration. The collapsed configuration is the configuration that is conventionally used during the process of crimping of a stent on a balloon. Typically, the balloon 10 includes no liquid or gas in the internal chamber of the balloon 10 and includes regions where the balloon material is folded over giving the balloon a crease-like appearance. Such collapsed configuration is typically the configuration of introduction and navigation of the balloon 10 in the bodily lumen or vascular system of a patient.

Figure 2B:
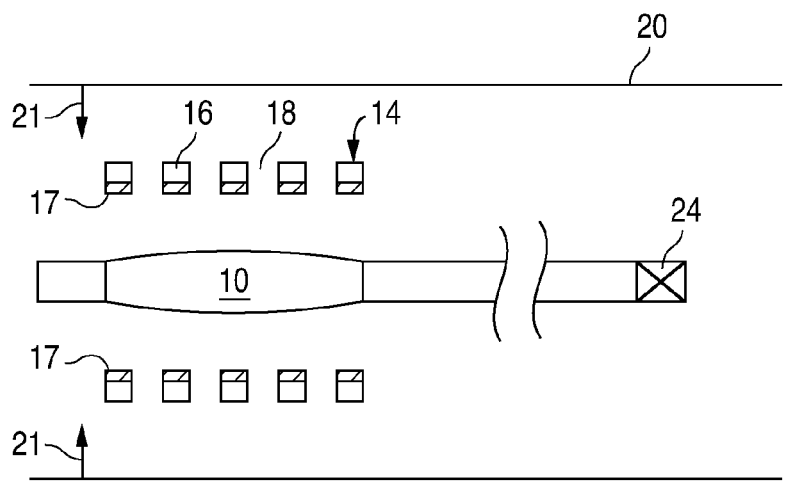
FIGS. 2B-C illustrate a crimping process of a stent onto an expandable member.

FIG. 2B illustrates a stent 14 is positioned over the balloon 10. The stent 14 is illustrated to have struts 16 separated by gaps 18 (as can also be seen in FIG. 1). In some embodiments, the diameter of the stent 14 as positioned over the collapsed balloon 10 is much larger than the collapsed diameter of the balloon 10. A retention layer 17 is disposed over the luminal surface of struts 16. As described in more detail below, in addition to the luminal surface, the retention layer 17 can be disposed over the sidewalls, abluminal surface, or both of struts 16. In other embodiments, as discussed in more detail below, the retention layer can be disposed over the surface of balloon 10 or both the surface of balloon 10 and struts 16. The crimping method described and illustrated in FIGS. 2B-C can also be applied to such other embodiments.

Figure 2C:
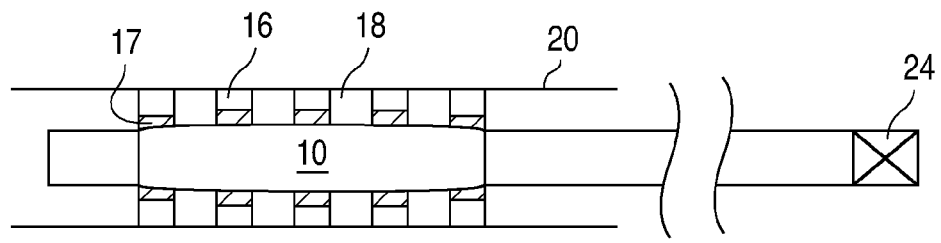

Additionally, as illustrated in FIG. 2C, the balloon 10 and the stent 14 are positioned in a crimping device 20. Stent 14 can be positioned in the device 20 and held in place by application of pressure from the crimping device 20. The device also heats the stent during crimping. The crimping device 20 can be any device used in the art or in this disclosed herein. In some embodiments, the device can apply pressure and heat simultaneously. The crimp device 20 then applies inward radial pressure to the stent 14 on the balloon 10, as shown by arrows 21. The stent 14 positioned over the balloon 10 is crimped to a reduced stent configuration (reduced crimped configuration), as illustrated in FIG. 2C.

Crimping can be defined as the process of mounting, fastening or securing a stent on a balloon. The stent can be fixedly carried by the balloon but can be deployed by inflation and subsequent withdrawal of the balloon in order to be implanted at a target site, such as a region of stenosis. The crimp process can include selectively, radially compressing or applying pressure for positioning a stent on a balloon of a catheter assembly or an expandable delivery member of a catheter assembly. The compression or radial pressure during crimping can be segmented or uniform across the length and/or circumference of the stent. The application of pressure by the crimping device 20 can be continuous or applied in an intermittent or step-wise fashion. In some embodiments, the crimping device can hold the pressure at the reduced crimped configuration for duration of time prior to release of pressure.

In embodiments of the present invention, the crimping is done at a temperature greater ambient that allows or facilitates adhesion or sticking of the retention layer 17 on the stent 14 onto the balloon 10. Ambient temperature can be between 20° C. and 30° C. In some embodiments, the retention layer 17 is heated to a temperature close to, at or above a Tg of a polymer material of the retention layer 17. In further embodiments, the retention layer 17 is heated to a temperature well above a Tg of a polymer material of the retention layer 17. In certain embodiments, the retention layer 17 is heated to a temperature close to, at or above a Tm of a polymer material of the retention layer 17. In other embodiments, the retention layer is heated to a temperature close to, at or above a Ts of a polymer material of the retention layer 17. In these or other embodiments, after crimping, the crimping device can hold the stent at an elevated temperature, which may be selected such that it is greater than, equal to, or less than the target temperature for the retention layer 17 or may be selected to specifically exclude temperatures greater than, equal to, or less than the target temperature. In some embodiments, the device crimps the stent while the stent is heated by other methods.

In some embodiments, the crimp temperature or temperature to which the retention layer is heated can be between ambient and 40° C., ambient and 50° C., ambient and 60° C., ambient and 70° C., or greater than 80° C. In certain embodiments, "well above" a Tg of a polymer material of the retention layer may mean more than 10° C., or more than 20° C., or more than 30° C. above the Tg. In general, the crimping temperature should be below a temperature at which damage is caused to stent or balloon which can affect their performance. The temperature can also be below a degradation temperature at which an active agent contained in the stent degrades.

In exemplary embodiments, for crimpers such as the sliding wedge design, the crimping temperature may be controlled by passage of a stream of dry air, or inert gas through the bore. This air can be heated or cooled by first passing it through a tube heater or chilled heat exchanger. The stent is loosely placed onto the catheter, and then the assembly is inserted into the bore of the crimper. The passage of air would rapidly equilibrate the stent delivery system to the crimp temperature. Continuously heated or cooled airflow would bring the crimping jaws to the desired temperature.

Alternative exemplary embodiments include heating or cooling the jaws of the crimper itself. Electrical heating elements can be installed into the crimper jaws. By appropriate placement of thermocouples and feedback controls, an elevated temperature can be maintained. Cooling of the crimper jaws can be accomplished by rendering them with passageways through which a cooling medium is pumped. This may also be used to heat the crimping jaws. If the jaws were composed of an electrically conductive material, application of an oscillating electric field can heat them via eddy currents. If the jaws were made of an IR transparent material, the stent on catheter can be thermostated by infrared radiation.

If the crimper is at ambient temperature, but the jaws themselves are of a material with low thermal conductivity, then processes can be considered where the stent is loosely applied to the catheter an is pre-equilibrated to a non-ambient temperature before crimping. As the stent is small, with a high surface area to volume ratio, it would have to be rapidly moved from the controlled temperature environment to the crimper to maintain the desired temperature. Heating in an incubator or oven, or cooling in a refrigerator can pre-equilibrate the stent to the desired temperature before crimping.

In further embodiments, the retention layer on the stent, balloon, or both can be heated to a target temperature by disposing a heated inflation fluid into the balloon. In such embodiments, the balloon can be partially inflated by the heated inflation fluid. The inflation fluid can be a liquid or gas. For example, the inflation fluid can be water, air, nitrogen, oxygen, argon, or carbon dioxide. A partially inflated configuration refers to a balloon state in which the balloon diameter is less than the balloon diameter used to deploy a stent at a treatment site in a bodily lumen.

Figure 3:
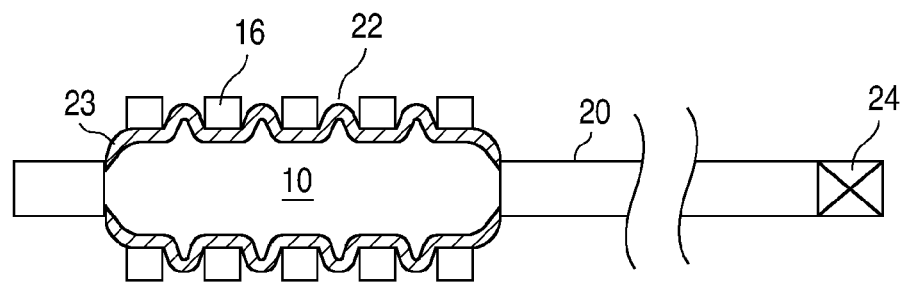
FIG. 3 depicts a stent with struts crimped onto a partially inflated balloon.

In one such embodiment, the fluid can be disposed into the balloon after crimping the stent onto the balloon in its collapsed configuration. The fluid can be disposed into the balloon while the crimper holds the stent in place over the balloon. Alternatively, the fluid can be disposed into the balloon and stent after removal of the stent from the crimping device while a sheath disposed over the stent holds the stent in place. FIG. 3 depicts a stent 14 with struts 16 crimped onto a partially inflated balloon 10. A retention layer 23 is disposed over the surface of balloon 10 and is heated by heated inflation fluid disposed or conveyed into balloon 10 as indicated by an arrow 31.

In some embodiments, the crimped stent can be delivered into a bodily lumen with the balloon in the partially inflated state. In one such embodiment, the inflation fluid can be removed from the balloon and replaced with inflation fluid at or near ambient temperature or below ambient temperature to cool the retention layer, stent, and balloon. The cooled inflation fluid can be less than 15° C., 10° C., or less than 0° C.

In other embodiments, a crimped stent can be delivered into a bodily lumen with the balloon in a collapsed or close to a collapsed configuration after heating the retention layer in the collapsed state. In such embodiments, the heated inflation fluid can be removed from the balloon. Radial pressure applied to the balloon, for example, by a crimping device can facilitate return of the balloon to the collapsed configuration. Residual inflation fluid can remain in the balloon. The stent and balloon may then be delivered with the balloon in a collapsed or near collapsed configuration.

In additional embodiments, the heated inflation fluid can be disposed into the balloon prior to crimping the stent into the balloon. The stent may then be crimped onto a partially inflated balloon. The stent and balloon may then be delivered with the balloon in the partially inflated state. Alternatively, the inflation fluid can be evacuated and pressure can be applied to the balloon to return the balloon to the collapsed configuration or close to the collapsed configuration. The stent and balloon may then be delivered with the balloon in a collapsed or near collapsed configuration.

In certain embodiments, stent retention can be further increased by crimping in such a way that the balloon wall protrudes from the gaps 18 between struts 16. The embodiments described above that including partial inflation of a balloon before or after crimping a stent over the balloon can be performed to provide protrusion of the balloon wall into the gaps between struts. FIG. 3 depicts a partially inflated balloon 10 in which the balloon wall or membrane protrudes out, as shown by protrusions 22, from the gaps 18 between the stent struts 16. Balloon 10 includes a retention layer 23 disposed over the balloon surface. In one embodiment, the protrusion 22 should not extend beyond the outer surface of the struts 16. Alternatively, the protrusion 22 can extend beyond the outer surface of the struts 16. This ensures that the balloon wall or membrane becomes adequately wedged, lodged, squeezed, or pinched between the struts 16 when the crimping process is completed. In such embodiments, the retention layer can be heated by a heated inflation fluid. Alternatively, the inflation fluid need not be heated above ambient temperature and the retention layer can be heated by other methods disclosed herein or method known in the art. Additionally, the retention layer can be heated by both the retention layer and other methods.

Figure 4:
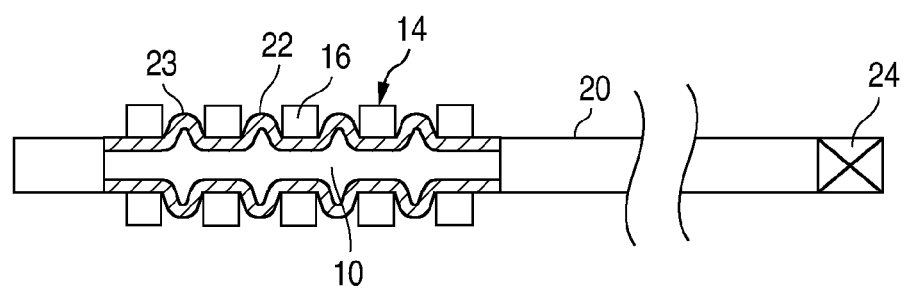
FIG. 4 depicts a stent disposed over the balloon after the inflation fluid has been evacuated.

As described above, the partially inflated balloon can be evacuated to return to a collapsed configuration or close to a collapsed configuration. In such embodiments, the balloon wall can remain at least partially protruding from through gaps 18 of struts 16. FIG. 4 depicts stent 14 disposed over the balloon 10 after the all or most of the inflation fluid has been removed to return the balloon to a collapsed or near collapsed configuration. As shown in FIG. 4, protrusions 22 of the balloon wall can extend into gaps 18 of struts 16.

In another embodiment, protrusions of the balloon wall between the struts can be formed in the absence of partial inflation of the balloon. Subsequent to crimping with or without heating, an outer sleeve can be disposed over the stent to restrain the crimped stent. Pressure and heat can be applied to the stent-balloon section simultaneously or subsequently to disposing the sleeve. Under this action, the balloon material deforms slightly, moving in between the struts. The heat can increase to temperature of the retention layer on the stent, balloon, or both to a target temperature to allow the retention layer to facilitate retention of the stent on the balloon.

In certain embodiments, the retention layer can be composed mostly, substantially or completely of a polymeric material that softens or becomes sticky to allow adhesion of a balloon and stent at a temperature between ambient and below the Tg or Ts of the stent substrate a layer between the substrate and the retention layer, the balloon base material below the retention layer, or both. In some embodiments, the retention layer can be composed mostly, substantially, or completely of a polymeric material having a lower Tm, Tg or Ts than the stent substrate a layer between the substrate and the retention layer, the balloon base material below the retention layer, or both. "Mostly" refers to greater than 50% and "substantially" refers to greater than 90%, 95%, or, 95%. In further embodiments, the polymeric material of the retention layer can have a Tg or Ts greater than human body temperature, which is about 37° C.

In some embodiments, the polymeric material of the retention layer can be a biodegradable polymer. In such embodiments, the polymeric material can start to degrade upon insertion into a bodily lumen. The layer can be designed so that the degradation does not significantly affect retention of the stent during delivery while allowing release of the stent upon deployment at an implant site in a bodily lumen. In additional embodiments, the polymeric material of the retention layer can be a water soluble polymer that starts to dissolve upon insertion into a bodily lumen during delivery, while allowing release of the stent upon deployment at an implant site in a bodily lumen.

Table 1 lists exemplary biodegradable polymer along with melting points and Tg's. John C. Middleton and Arthur J. Tipton, *Synthetic Biodegradable Polymers as Medical Devices*, Medical Plastics and Biomaterials Magazine, March 1998. In an exemplary embodiment, a stent scaffolding is made from poly(L-lactide) polymer, which has a Tg of 60 to 65° C. The retention layer material may be selected such that it softens or partially melts, or becomes sticky at a temperature greater than ambient or greater than body temperature, but less than about 60° C. In exemplary embodiments, the retention layer can include various oligomers or low molecular (Mw is less than 50 kg/mol) homo-polymers and copolymers such as PCL, PTMC, PDO, PHB, PCL-co-PTMC, PCL-co-PDO, PCL-co-PDLA, PCL-co-PTMC, PCL-co-PEG-co-PCL.

TABLE 1

Melting points of biodegradable polymers.

| Polymer | Melting Point (° C.) | Glass-Transition Temp (° C.) |
|---|---|---|
| Polyglycolide (PGA) | 225-230 | 35-40 |
| Poly(L-lactide) (PLLA) | 173-178 | 60-65 |
| Poly(DL-lactide) (PDLLA) | Amorphous | 55-60 |
| Polycaprolactone (PCL) | 58-63 | (−65)-(−60) |
| Polydioxanone (PDO) | N/A | (−10)-0 |
| Poly(glycolide-trimethylene carbonate) (P(GA-TMC)) | N/A | N/A |
| 85/15 PDLLA-PGA Blend | Amorphous | 50-55 |
| 75/25 PDLLA-PGA Blend | Amorphous | 50-55 |
| 65/35 PDLLA-PGA Blend | Amorphous | 45-50 |
| 50/50 PDLLA-PGA Blend | Amorphous | 45-50 |

In additional embodiments, the retention layer can be composed of a water soluble polymer. Representative examples of water-soluble polymers for the retention layer include, but are not limited to, water soluble polyurethane adhesives made from a reaction of a diisocyanate with a polyol such as poly(ethylene oxide), poly(vinylmethylether) or poly(2-ethyl-2-oxazoline); polymers and copolymers of crylamide, acrylic acid, malelic acid, vinyl acetate, crotonic acid, vinylimidazole, maleic anhydride and vinylpyrrolidone, polysaccharide, hydroxyethylcellulose, carboxymethylcellulose, polymeric salts, polyvinyl alcohol, polyethylene glycol, polyethylene oxide, glucose, dextran, dextrose, lactose, gamma globulin, ambumin, and combinations thereof.

In various embodiments, the retention layer can be disposed over the surface of the stent to allow adhesion of the stent to a surface of a balloon on which the stent is crimped. As discussed above, in certain embodiments, the retention layer can be disposed over all or a portion of a surface of the stent struts. As shown in FIGS. 2B-C, the retention layer can be disposed over the luminal surface with the sidewall and abluminal surfaces being free or substantially free of the retention layer.

Figure 5:
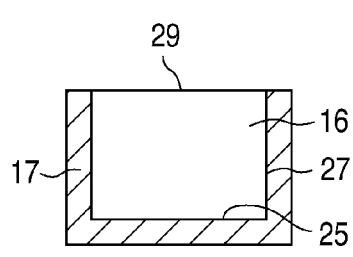
FIGS. 5 and 6 depict embodiments of a retention layer over a stent strut.
Figure 6:
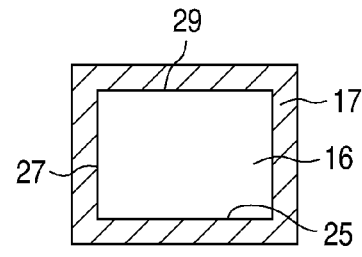

As shown in FIG. 5, the retention layer 17 can be disposed over the luminal surface 25 and sidewall surfaces 27 with the abluminal surface 29 free or substantially free of the retention layer. "Substantially free" may for correspond to less than 10% coverage. In some embodiments, the retention layer can be over all or substantially all of the luminal, abluminal, and sidewall surfaces of the stent. FIG. 6 depicts a cross-section of a strut 16 of stent with a retention layer 17 disposed over the luminal, abluminal, and sidewall surfaces of strut 16 of the stent. "Substantially all" can correspond to at least 90% coverage.

Figure 7:
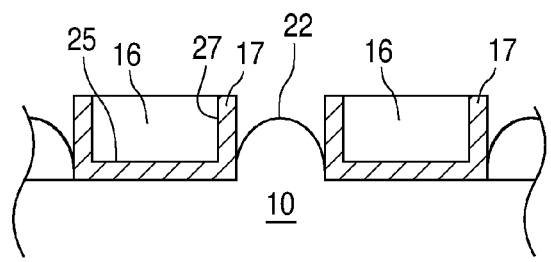
FIG. 7 depicts an expanded view of struts crimped onto the surface of a balloon.

In embodiments with the balloon wall protruding through gaps in the stent, a retention layer on the sidewalls of a stent can further facilitate retention of the stent to the balloon. FIG. 7 depicts an expanded view of struts 16 crimped onto the surface of a balloon 10. Struts 16 have a retention layer 17 on luminal surface 25 and sidewall surfaces 27 of the strut 16. The surface of protrusions 22 adhere to retention layer 17 on sidewall surface 27 of strut 16.

The retention layer may be applied to the stent by methods know in the art, for example, by coating methods such as spraying or dipping. A coating material including the polymer material of the retention layer dissolved in a solvent may be applied to the surface of the stent. The solvent is then removed through evaporation leaving the polymeric retention layer. Selective coating on the luminal surfaces and sidewall surfaces of the stent can be accomplished by methods know in the art such by masking portions during spraying.

Figure 8:
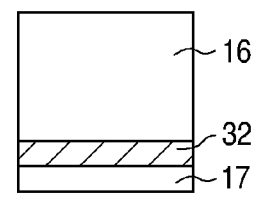
FIG. 8 depicts a cross-section of a strut a strut with a retention layer disposed over a drug delivery layer.

In further embodiments, the retention layer can also be a drug delivery layer with a drug mixed or dispersed within the polymeric material of the retention layer. Alternatively, the retention layer can be disposed over a drug-polymer layer. FIG. 8 depicts a cross-section of a strut 16 with retention layer 17 disposed over a drug delivery layer 32 with a drug (not shown) mixed or dispersed within a polymer material. The polymer material of the drug delivery layer can be the same or different than the polymer material of the retention layer. Such an embodiment allows more flexibility in choice of the polymer materials for the retention layer and drug delivery. The retention layer can also serve as a drug release rate controlling layer.

As discussed above, embodiments of the invention include a retention layer over at least a portion of the expandable member of balloon on which a stent is disposed. The retention layer over the balloon can be in addition to or an alternative to the retention layer on the stent. The balloon can be coated using the same or similar coating methods described above for a stent. In some embodiments, the balloon can be coated in a collapsed configuration. In such an embodiment, portions of the balloon surface that are hidden due to folding are free of the retention layer.

Figure 9A:
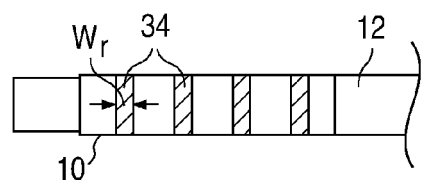
FIGS. 9A-B depict embodiments of a retention layer selectively disposed over a balloon surface.
Figure 9B:
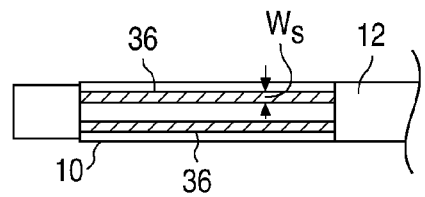

In certain embodiments, the retention layer can be selectively disposed over the balloon surface in the collapsed configuration or the inflated configuration. In several of such embodiments, the retention layer can be selectively disposed over surface of the balloon in the collapsed configuration so that some portions of the surface are free of the retention layer. In one such embodiment, the retention layer can be disposed as rings around the circumference of the balloon. Such rings may be disposed so as to maximize contact of the luminal surface of rings of the stent. In other such embodiments, the retention layer can be disposed as longitudinal strips along the cylindrical axis of the balloon. FIG. 9A depicts an axial cross-section of balloon 10 with retention layer rings 34 disposed at several axial positions along balloon 10. FIG. 9B depicts an axial cross-section of balloon 10 with retention layer strips 36 disposed at two circumferential positions around balloon 10. The width (Wr) of rings 34 and width (Ws) of strips 34 can be optimized to obtain a selected degree of retention of a stent on balloon 10.

In some embodiments, the thickness of the retention layer may be adjusted to obtain a desired decree of retention. In exemplary embodiments, the thickness may be from 1-10 μm, 10-20 μm, 20-30 μm, 30-40 μm, 40-50 μm, or greater than 50 μm. The thickness of the coating may be adjusted according to the holding power of the polymer coating. For example, a polymer material that provides a higher degree of adhesion per unit weight may require a thinner coating.

In further embodiments, a method of stent retention can include disposing a sheath over a stent having a retention layer on at least a portion of its luminal surface. In some embodiments, the balloon outer surface can have retention layer. In one embodiment, the stent may be in an as-fabricated configuration. An "as-fabricated" condition can correspond to the stent in an uncrimped condition with a diameter the same as the stent after cutting the stent from a tube. In another embodiment, the stent may be in a crimped condition and is restrained at a crimped diameter by the sheath. The method may further include disposing the stent and sheath over a delivery balloon which may alternatively or additionally include a retention layer.

Figure 10A:
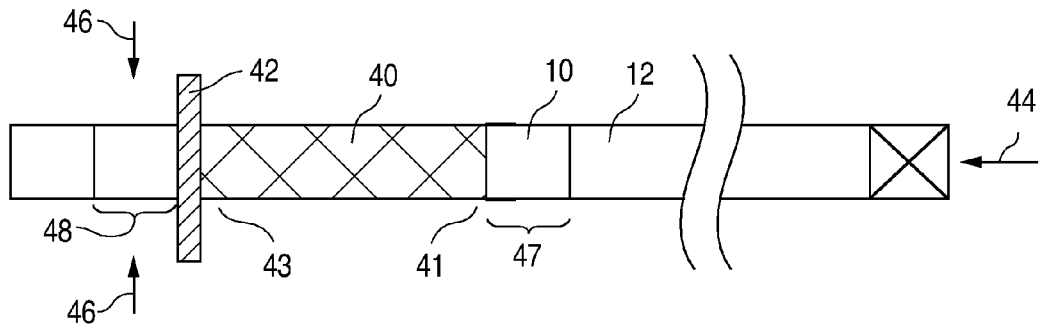
FIGS. 10A-C depict a stent retention method.
Figure 10B:
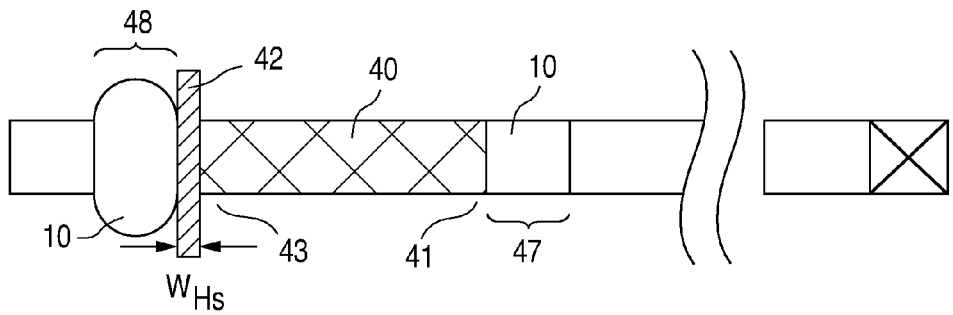
Figure 10C:
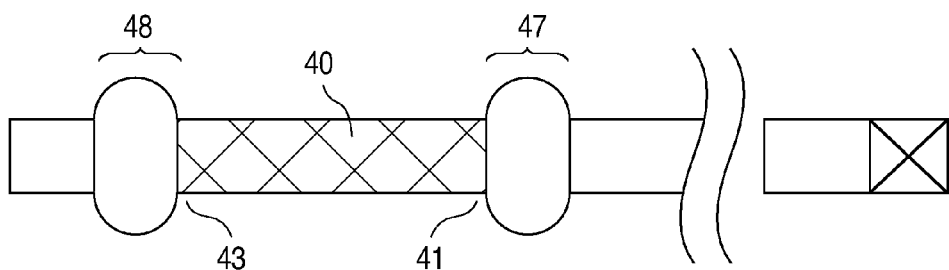

The above-described retention method is further illustrated in FIGS. 10A-C. FIG. 10A depicts a sheath 40 over a stent (not shown) disposed over a balloon 10. A distal section 48 and a proximal section 47 are not covered by sheath 40 and the stent. A heat shield 42 is disposed at a distal end of sheath 40 and the stent. The heat shield 42 can be a disk-shaped object with a hole though its center to allow positioning over balloon 10. Distal section 48 is heated, for example, by a nozzle blowing a heated gas, as shown by arrows 46. An inflation fluid is conveyed into balloon 10, shown by an arrow 44. The distal section 48 inflates as shown in FIG. 10B. Heat shield 42 can be a material with a relatively low thermal conductivity such as rubber, plastic, or silicone.

The heat shield 42 reduces heat transfer to balloon 10, sheath 40, and the stent proximal to the distal section 48 to protect them from thermal damage. However, the heat shield 42 allows heat to be transferred to increase a temperature of the retention layer on the stent in a region 43 proximal to heat shield 42. In some embodiments, the temperature required to inflate distal section 48 of balloon 10 is higher than a target temperature for the retention layer. For example, the temperature of the distal section 48 and proximal section 47 may be increased to between 60 and 100° C., 75 and 95° C., 80 and 90° C., or more narrowly about 85° C. Such temperature ranges may be applicable for typical stent delivery balloons, for example, balloons made from such materials as elastomeric materials such as Pebax® polyether block amides (from Arkema, Inc. of Philadelphia, Pa.).

The heat shield can be designed to allow heat transfer such that the increase in temperature of the retention layer is sufficient to allow the retention layer to increase the adhesion of the stent to the balloon. For example, a heat shield material with a suitable thermal conductivity can be selected, the width (Whs) of the heat shield 42 can be varied, or both to provide the desired heat transfer to the retention layer. In some embodiments, the retention layer is heated to a temperature close to, at or above a Tm or Tg of a polymer material of the retention layer. In further embodiments, the retention layer is heated to a temperature well above a Tg of a polymer material of the retention layer. In other embodiments, the retention layer is heated to a temperature close to, at or above a Ts of a polymer material of the retention layer.

In further embodiments, the inflation fluid can be heated to increase the temperature of the retention layer on the stent or balloon 10 to provide increased adhesion along their whole length. The above-described process is repeated for the proximal section 47 of balloon 10. The heat shield 42 allows heat to be transferred to increase a temperature of the retention layer on the stent or balloon in a region 41 distal to a heat shield positioned at proximal end of sheath 40 and the stent.

FIG. 10C depicts sheath 40 and stent over balloon 10 with distal section 48 and proximal section 47 of balloon 10 inflated. Inflated section 48 and 47 of balloon 10 serve to increase retention of the stent and sheath 40 on the balloon. Additionally, the retention layer in distal region 43 and proximal region 41 further facilitates adhesion of the stent on balloon 10.

Further embodiments of facilitating stent retention can include a water soluble or degradable sheath positioned over the stent. The sheath can be disposed over the stent such that the sheath is capable of retaining a stent disposed over a support or balloon as the stent and balloon are conveyed through a lumen during delivery of the stent to an implant site. The sheath can be longer than the stent, the same length as the stent, or shorter than the stent. As the stent and balloon are conveyed through the lumen, the sheath degrades or dissolves. In some embodiments, dissolution or erosion of the sheath provides lubrication between the delivery system and lumen walls, facilitating delivery of the stent.

In some embodiments, the sheath can include an active agent or drug. The drug can be mixed or dispersed within the sheath material or in a coating or layer of the sheath. The drug or active agent can be released during delivery, after deployment, or both. The drug can include an anti-inflammatory agent, anti-proliferative agent, antithrombogenic agent, or combinations thereof.

In certain embodiments, the sheath material can have a Tg or Ts less than an ambient temperature, between ambient and body temperature, or between body temperature and the Tg of the stent scaffolding material. In some embodiments, the sheath can be heated during or after positioning the sheath on the stent to a temperature close to, at or above a Tm or Tg of a polymer material of the sheath or to a temperature close to, at or above a Ts of a polymer material of the sheath so that the sheath sticks to the stent. The sheath material can include any of the polymeric materials listed herein for the retention layer. In additional embodiments the stent can include a retention layer over at least an abluminal layer of the stent which further facilitates adhesion of the sheath to the stent.

In certain embodiments, the sheath can be adapted to provide for or facilitate retention of the stent during a selected time frame of the delivery. As the sheath dissolves or erodes, the mechanical properties of the sheath degrade. In one embodiment, the sheath facilitates retention at least up to a time of deployment. In other embodiments, the sheath can be adapted to fail or fracture prior to deployment with the stent being retained on the balloon by other means. In additional embodiments, the sheath is completely or almost completely dissolved or eroded prior to deployment. In some embodiments, when the stent is deployed, the balloon expansion ruptures the sheath and allows the stent to expand into the lumen walls at the implant site. In other embodiments, the stent presses the sheath into the lumen walls and the sheath erodes away after deployment. A sheath including an active agent can continue to release the active agent after deployment.

In other embodiment, the thickness of sheath wall can be varied to provide retention during a desired time frame during delivery. Additionally, a material can be selected having mechanical properties such as a strength and modulus to facilitate or provide retention during a desired time frame. In exemplary embodiments, the sheath can have a wall thickness of 3-20 μm, 20-50 μm, 50-70 μM, or 70-100 μm.

In some embodiments, the sheath can be disposed over a stent in a crimped state after crimping the stent onto a balloon. In other embodiments, the sheath can be disposed onto a stent in an uncrimped or as-fabricated state. In further embodiments, the embodiments of the water soluble or degradable sheath described herein can be used in embodiments described in FIGS. 10A-10C.

In further embodiments, a sheath for disposing on the stent can have an inner diameter such that the sheath has a tight fit on the stent so that the sheath retains the stent on a balloon during delivery through a lumen. In one such embodiment, the inner diameter of the sheath is the same or substantially the same as the stent.

In other embodiments, the sheath can initially have a diameter such that it is loosely disposed over the stent with the inner diameter of sheath greater than outer diameter of stent. The stent can be disposed over a balloon or a non-inflatable stent support during positioning of the sheath on the stent. The sheath can then be heated to cause the stent to shrink radially so that the sheath is in contact with the stent to provide a tight fit over the stent. In additional embodiments, the sheath can be heated to a temperature to cause the sheath to stick to the stent, for example, above the Tg of the sheath.

Figure 11A:
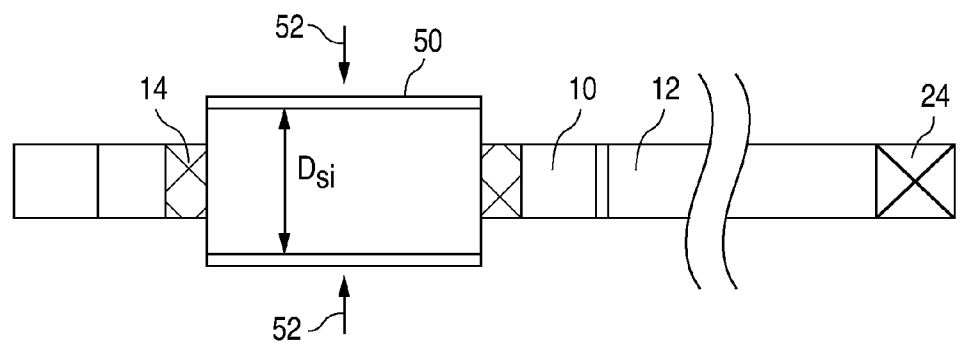
FIGS. 11A-B depict a method of disposing retention sheath over stent.
Figure 11B:
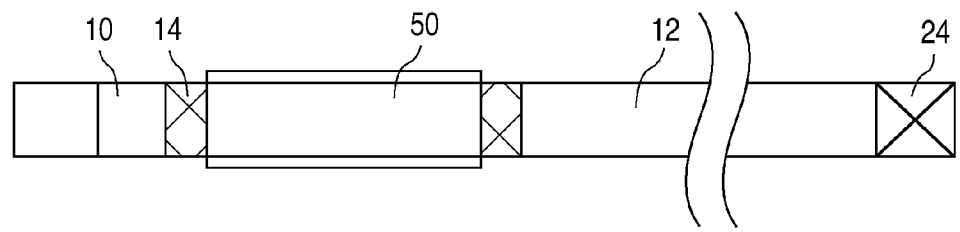

FIG. 11A depicts a flattened view of a stent 14 crimped over a balloon 10 on a catheter 12 with the stent 14 shown to cover the outside surface of balloon 10. Sheath 50 is loosely disposed over stent 14 and balloon 10 with an inner diameter (Dsi) greater than an outer crimped diameter of stent 14. Although sheath 50 is shown to have an axial length shorter than stent 14, sheath 50 can be the same length or longer than stent 14. Sheath 50 is heated by a heat source (not shown) which can be a nozzle directing heated gas stream at sheath 50 as shown by arrows 52. Sheath 50 is heated to a temperature that causes it to shrink radially to a diameter such that sheath 50 has a tight fit over stent 50. Additionally, in some embodiments the sheath material becomes soft and sticky and sticks to a surface of the stent and facilitates adhesion of the sheath to the stent.

Figure 12:
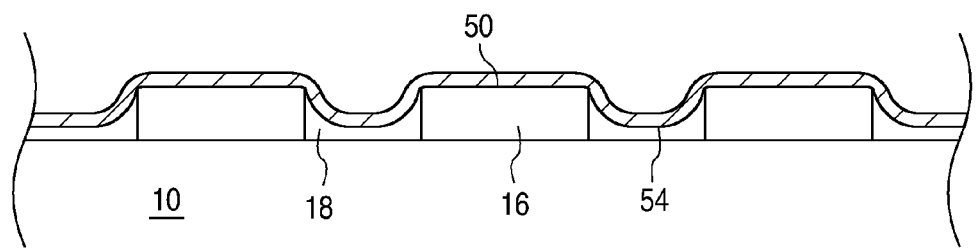
FIG. 12 depicts an expanded view showing a cross-section of struts of a stent crimped onto a balloon.

In some embodiments, the sheath wall becomes flexible enough during positioning of the sheath over the stent such that the walls of the sheath protrude through gaps in the stent. FIG. 12 depicts an expanded view showing a cross-section of struts 16 of a stent crimped onto a balloon 10. The wall of sheath 50 is shown to be disposed in contact with struts 16 with the wall protruding as shown by index number 54 through the gaps 18 of the stent. The walls sheath 50 can stick both the luminal surface and sidewall surface of the struts 16. In some embodiments, the wall can deform enough that the wall makes contact with the outer surface of balloon 10, further enhancing retention of the stent on balloon 10.

Generally, a stent may be formed, for example, from a tube or a sheet rolled into a tube. The sheet or tube, for example, may be formed by various methods known in the art such as extrusion or injection molding. A pattern may then be cut into the polymeric tube by laser cutting or chemical etching to form the stent.

Additionally, as mentioned above, a stent fabricated from embodiments of the stent described herein can be medicated with an active agent. A medicated stent may be fabricated by coating the surface of the polymeric scaffolding with a polymeric carrier that includes an active or bioactive agent or drug.

Embodiments of the present invention described herein may be applied to devices including, but not limited to, balloon expandable stents, self-expanding stents, and stent-grafts. In the case of a self-expanding stent, the stent can be crimped over a support, such as a catheter. The stent is used to open a lumen within an organ in a mammal, maintain lumen patency, or reduce the likelihood of narrowing of a lumen.

The method according to the invention can be used to increase retention in both polymeric and metallic stents. In one embodiment, the polymer for use in forming the stent scaffolding and/or the stent coating may be configured to degrade after implantation by fabricating the stent either partially or completely from biodegradable polymers.

In general, polymers for use in fabricating a substrate of a stent or a coating for a stent can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat a stent include, but are not limited to, poly (N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating a stent include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. A non-polymer substrate of the stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent delivery assembly, comprising:
    disposing a sheath over a stent, the stent comprising a stent substrate;
    disposing the stent and the sheath over a central axial section of an expandable member, leaving a distal axial section and proximal axial section of the expandable member uncovered by the stent and the sheath;
    inflating the distal axial section, wherein only the distal axial section is directly heated; and
    inflating the proximal axial section, wherein only the proximal axial section is directly heated,
    wherein either the stent comprises a retention layer disposed over at least a portion of the stent substrate, or the expandable member comprises a retention layer disposed over at least a portion of the expandable member, the retention layer comprising a polymeric material, and wherein the retention layer is heated to a temperature close to, at or above a Tm, a Tg, or a Ts of the polymeric material of the retention layer, wherein the inflated distal axial section, inflated proximal axial section, and retention layer facilitate adhesion of the stent to the expandable member.

2. The method of claim 1, wherein the stent substrate comprises a biostable polymer, biodegradable polymer, or a combination thereof.

3. The method of claim 2, wherein the polymeric material of the retention layer has a lower Tg or Ts than the polymeric material of the stent substrate.

4. A method of fabricating a stent delivery assembly, comprising:
    disposing a sheath over a stent, the stent comprising a stent substrate;
    disposing the stent and the sheath over a central axial section of an expandable member, leaving a distal axial section and proximal axial section of the expandable member uncovered by the stent and the sheath;
    inflating the distal axial section, wherein the distal axial section is heated; and
    inflating the proximal axial section, wherein the proximal axial section is heated,
    wherein either the stent comprises a retention layer disposed over at least a portion of the stent substrate, or the expandable member comprises a retention layer disposed over at least a portion of the expandable member, the retention layer comprising a polymeric material, and wherein the retention layer is heated to a temperature close to, at or above a Tm, a Tg, or a Ts of the polymeric material of the retention layer, wherein the inflated distal axial section, inflated proximal axial section, and retention layer facilitate adhesion of the stent to the expandable member; and
    wherein a heat shield is disposed only at a distal or proximal end of the stent and sheath to reduce heat transfer to the stent and sheath.

* * * * *